United States Patent [19]

Smith et al.

[11] 4,087,518

[45] May 2, 1978

[54] FOAMING AND CONDITIONING PROTEIN-CONTAINING DETERGENT COMPOSITIONS

[75] Inventors: Rory James Maxwell Smith, Rowlands Gill, England; Gordon John Mackie, Strombeek-Bever, Belgium

[73] Assignee: The Procter & Gamble Company, Cincinnati, Ohio

[21] Appl. No.: 665,849

[22] Filed: Mar. 11, 1976

[30] Foreign Application Priority Data

Mar. 17, 1975 United Kingdom .............. 11003/75

[51] Int. Cl.$^2$ .............................................. A61K 7/06
[52] U.S. Cl. ................................ 424/70; 252/DIG. 2; 252/DIG. 13; 252/142; 252/554; 424/DIG. 2; 424/359; 252/DIG. 3; 252/545; 252/550; 252/551; 252/558
[58] Field of Search .................... 424/DIG. 2, 70, 359; 252/DIG. 2, DIG. 3, DIG. 13, 545, 550, 142, 551, 554, 558

[56] References Cited

U.S. PATENT DOCUMENTS

| | | | |
|---|---|---|---|
| 1,965,008 | 7/1934 | Sponsel et al. | 260/117 |
| 2,113,819 | 4/1938 | Tucker | 260/112 R |
| 2,282,001 | 5/1942 | Russell et al. | 260/117 |
| 2,363,892 | 11/1944 | Monier | 260/117 |
| 3,340,153 | 9/1967 | Kast | 424/359 |
| 3,548,056 | 12/1970 | Eigen et al. | 424/171 |
| 3,642,977 | 2/1972 | Hewitt | 424/70 |
| 3,738,913 | 6/1973 | Johnsen et al. | 424/359 X |
| 3,787,337 | 1/1974 | Goodwin | 252/545 |
| 3,824,228 | 7/1974 | Eckert et al. | 260/117 |
| 3,898,129 | 8/1975 | Fujimoto et al. | 252/544 X |
| 3,898,186 | 8/1975 | Mermelstein et al. | 252/546 X |
| 3,904,748 | 9/1975 | Eckert et al. | 424/70 |
| 3,907,580 | 9/1975 | van Ham | 424/359 X |
| 3,954,725 | 5/1976 | Johnsen et al. | 260/112 R |

FOREIGN PATENT DOCUMENTS

| | | | |
|---|---|---|---|
| 278,250 | 1/1970 | Austria | 424/70 |
| 877,909 | 8/1971 | Canada | 424/359 |
| 120,311 | 5/1971 | Denmark | 260/123.5 |
| 1,157,928 | 6/1978 | France | 424/70 |
| 2,053,195 | 4/1971 | France | 424/70 |
| 722,596 | 7/1942 | Germany | 424/359 |
| 1,192,370 | 5/1965 | Germany | 424/71 |
| 2,151,750 | 4/1973 | Germany | 424/70 |
| 1,057,418 | 2/1967 | United Kingdom | 424/70 |
| 1,122,076 | 7/1968 | United Kingdom | 424/70 |
| 1,224,798 | 3/1971 | United Kingdom | 424/70 |
| 1,254,309 | 11/1971 | United Kingdom | 424/70 |
| 1,276,960 | 6/1972 | United Kingdom | 424/70 |

OTHER PUBLICATIONS

Schimmel Briefs, No. 348, Schimmel & Co., Newburgh, Jan. 1965, 2 pp,

*Primary Examiner*—Albert T. Meyers
*Assistant Examiner*—Vera C. Clarke
*Attorney, Agent, or Firm*—Richard C. Witte; Thomas H. O'Flaherty; David F. Chalmers

[57] ABSTRACT

Liquid detergent compositions are provided containing a modified protein of pI > pH6 and a mixture of alkyl benzene sulphonate and auxiliary surfactants in which the ratio of alkyl benzene sulphonate to the auxiliary surfactant is greater than 1.5:1. The compositions show enhanced mildness to skin relative to detergent compositions in which the surfactants are at lower ratios.

10 Claims, No Drawings

FOAMING AND CONDITIONING PROTEIN-CONTAINING DETERGENT COMPOSITIONS

FIELD OF THE INVENTION

This invention relates to compositions which protect keratinous material, such as skin or hair, from the deleterious effects of detergents or other harsh materials such as solvents, and from adverse climatic conditions.

BACKGROUND OF THE INVENTION

The deleterious effects of compositions containing surfactants upon keratin are well-known. These effects are caused, it is thought, by penetration of the surfactant into the keratin surface leading to "leaching out" of oils and moisturising components essential for good condition of the keratin. This penetration by surfactant and "leaching out" of essential oils also affects the ability of the keratin, particularly in the case of skin, to retain water within the tissue and this again leads to poor condition of the keratinous material.

Compositions containing surface-active agents and providing greatly enhanced conditioning benefits over previous formulations, are described in the commonly assigned German Patent Application No. DOS 2434063 filed July 16, 1974, and published on Feb. 6, 1975, the disclosures of which are specifically incorporated herein by reference. According to this Application, certain proteins modified in specific ways have been found to improve the emolliency of detergent compositions containing them and such compositions successfully meet the twin objectives of improved mildness and conditioning characteristics, with maintained lathering and detergency characteristics.

One problem posed by the use of proteins in detergent compositions, however, stems from the fact that proteins, even at relatively low concentration, can have quite large effects on the physical characteristics of the compositions, despite the fact that their basic cleaning characteristics may be substantially unimpaired. Such effects may take, for instance, the form of increased viscosity of liquid formulations or decreased ease of solution of granular formulations. Clearly, it would be of advantage to increase the conditioning benefit/protein level efficiency so as to either increase the maximum level of conditioning benefit inherent in a given type of protein formulation, or so as to achieve a given level of conditioning benefit from a reduced content of the protein. In the latter case, conditioning and detergency characteristics may be optimized without having an undue effect on the physical characteristics of the base detergent formula.

Thus, one object of the present invention is the provision of protein-containing detergent compositions having significantly improved emolliency and conditioning benefits, in which the efficiency of such benefits for a given level of protein is improved. A further object of the invention is the provision of protein-containing detergent compositions in which the effect of the protein on the physical characteristics of the detergent composition is reduced.

SUMMARY OF THE INVENTION

Accordingly, the present invention provides a foaming and conditioning detergent composition comprising:

(a) an alkyl benzene sulphonate in which the alkyl group contains from eight to 18 carbon atoms in a straight or branched chain configuration;
(b) an auxiliary natural or synthetic anionic, nonionic, amphoteric or zwitterionic surfactant;
(c) a modified protein having an isoionic point greater than pH6, the weight ratio of (a) to (b) being in the range from 1.5:1 to 10:1 and the weight ratio of (a) + (b) to (c) being in the range from 4:1 to 500:1.

In this specification, a modified protein means a nonenzymic product, other than a derived protein, obtained in one or more stages by chemical or biochemical modification of a precursor protein, a precursor protein being chosen from natural, derived, synthetic or biosynthetic protein, and a derived protein being the product of hydrolytic, ammoniolytic, enzymatic, reductive or thermal degradation of a protein material.

DETAILED DESCRIPTION OF THE INVENTION

(a) The Modified Protein

A modified protein component of the present invention is defined as the product of a reaction in which the carboxylic or primary amino groups of a precursor protein have been modified to give at least one of the functional species:

| | | | |
|---|---|---|---|
| —SR | —OR | —C—COOR | —NHR |
| —S—S—R | | —C—CONHR | —NR$_2$ |
| | | —C—CONR$_2$ | | wherein R is an alkyl, alkenyl, aryl, cycloalkyl or heterocyclyl group containing not more than eight carbon atoms and up to two hetero atoms which may be the same or different. Modified proteins of the present invention have an isoionic point greater than pH 6.0 and a molecular weight of at least 5000. Of the above proteins preferred are those in which R has the formula:

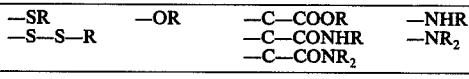

in which $Q^1$ is $R^1$, $OR^1$, $NHR^1$ or $NR^1_2$ in which $R^1$ is a hydrogen atom or an alkyl or alkenyl moiety, $p$ is 0 or 1 and $q$ is from 0 to (5-p).

Preferred classes of modified protein falling within the above definitions are those in which R is represented by:

(1) CH$_2$—CH(OH)—(CH$_2$)$_r$—H in which $r$ is from 0 to 4, (2) CH$_2$—(CH$_2$)$_r$—H in which $r$ is from 0 to 3, and

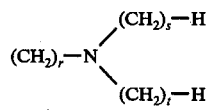 3)

in which $r$ is from 1 to 4 and $s$ and $t$ are each from 0 to 3.

The protein modification may be carried out by the normal methods used in preparing proteins having functional substituents. The reactive centres at which modification is performed are protein side-chains comprising carboxylic acid or primary amino groups, although simultaneous modification of other reactive centres such as sulphydryl, aliphatic or phenolic hydroxy, imidazole or guanidino groups, may also occur. One preferred modified protein has, as substituents, carboxylic ester or amide groups derived from the carboxylic acid groups of the unmodified substrate. The ester may be obtained from the protein and the appropriate alcohol by suspending the protein in the anhydrous alcohol at a temperature between 0° and 25° and at an acid concentration of 0.02 to 0.1M for several days or at 65° to 95° C. for between 1 and 5 hours. Alternatively, hydroxyalkyl esters may be prepared by reaction of the protein with an epoxide, for example but-1-ene oxide. In reactions of this type esterification may be accompanied by hydroxyalkylation of other reactive species, for example primary amino groups. The extent of such N-hydroxylalkylation depends primarily on the pH conditions employed. If the pH of the reaction medium is held in the acid region during the course of the reaction, then the degree of N-hydroxyalkylation is rather less than if the pH is allowed to rise during the reaction. Esterified products may also be prepared by reaction with diazoacetic esters or amides. Amides may be produced from the protein carboxylic acid groups by reaction with a water-soluble carbodiimide and an amine. This simultaneously may lead to modification of phenolic groups of tyrosine or sulphydryl groups of cysteins, giving O-aryl isoureas and S-alkyl isothioreas respectively.

The precursor proteins suitable for use, after modification in the compositions of the invention, may be chosen from natural, derived, synthetic or biosynthetic proteins. Natural proteins may be of either animal or vegetable origin and include simple and conjugated protein.

Typical natural proteins include intracellular proteins and globular proteins such as those present in blood plasma and milk, as well as solubilized collagen and protein isolates from nuts, cereals etc. such as soybean isolate, peanut protein, cotton seed protein etc. Derived proteins may be obtained from many sources, for instance by hydrolytic, ammoniolytic, thermal or enzyme degradation of globular or structural proteins such as keratin, collagen, fibrinogen, myosin, whey, egg white, casein or vegetable proteins such as those obtained from cereals, nuts, soybean curd or the protein-rich residues from seed-oil manufacture.

Protein primary amino group modification takes place primarily at lysine groups and, desirably, the modified protein should have at least 4 gms., preferably at least 6 gms. of lysine per 100 gms. of protein. Suitable precursor proteins in this class include the milk proteins, casein and whey, and egg white proteins (primarily ovalbumin) or derived proteins prepared therefrom. Another class of modified proteins comprise at least 20 gms. of aspartyl and glutamyl groups, in total, per 100 gms. of protein. Soybean isolates or derived soyproteins fall into this class.

Particularly preferred proteins for use in the compositions of the invention have characteristic values of molecular weight and isoionic-point pH and these will now be discussed in some detail.

It will be appreciated that the molecules of a protein vary widely in their size and complexity and that the molecular weight of a protein is necessarily an imprecise quantity. The molecular weight of a protein may be specified by defining the molecular weight distribution of the molecules of the protein, but it is usual to define, instead, the average molecular weight of the protein sample because it is an average molecular weight which is measured by most physical techniques. Such an average is only an approximate guide, however, to the actual molecular weight distribution of the sample. Also, it should be appreciated that the average molecular weight as measured may vary from one measuring technique to another although the differences between the results of the various techniques generally diminish towards lower moledular weights. In this specification, one method employed for determining average molecular weights of proteins (for molecular weights greater than about 5000) makes use of viscometric measurements of buffered protein solutions. The intrinsic viscosity of a buffered protein solution is known to be primarily dependent upon the overall length of the protein coil and to be relatively independent of the nature of the sidechain and end groups of the protein. There is, therefore, a relationship between intrinsic viscosity and the average molecular weight of the protein, which may be expressed as:

$$[\eta] = K \cdot M^a \quad \text{[Staudinger's Equation]}$$

where $K$ and $a$ are constants for a particular source of protein. It is thus straightforward to determine molecular weights from viscosity measurements, knowing $K$ and $a$, and this is fully described in Macromolecular Chemistry of Gelatin, page 72, by A. Veiss, and in Biochimica et Bisphysica Acta, 57, 222 – 9 (1961) by J. Bello, H. R. Bello, and J. R. Vinograd. This description is hereby incorporated herein by reference.

The above-described viscosity method is not very accurate for molecular weights below about 5000 and an ultracentrifuge measurement technique is more suitable for this range. However, comparison of the two techniques have shown only small differences in observed molecular weights up to values of 50,000–80,000.

When measured by the above methods, modified proteins of animal origin in accordance with the invention, e.g. modified gelatins, have an average molecular weight in the range from 5,000–200,000 more especially in the range 20,000–100,000. Modified proteins of vegetable origin, e.g. soyprotein, have molecular weights up to 50,000 preferably from 5,000–10,000.

In the modification of protein carboxylic acid functions, for instance by esterification, hydroxyalkylation or amidation of animal derived proteins, it is preferred that at least 20%, more preferably at least 40% of the free carboxylic acid groups are reacted. The isoionic point of such modified proteins, i.e. the pH at which equal concentrations of protein anions and cations exist in solution will preferably be greater than 7.2 and desirably greater than 8.0 or even 9.0. The detergent compositions based on these proteins are additionally characterized, in general, by having an in-use pH, i.e. the pH of the composition itself or of an aqueous solution or dispersion at in-use concentration, of less than (pI − 1.4) where pI is the isoionic point pH of the protein.

The isoionic point pH of the protein may be determined in the following manner. Amberlite acid resin (IR 120) and base resin (IR 400) are washed with several volumes of water, filtered and mixed in the ratio 0.4:1. A solution (20 mls.) of protein (3%) and urea (20%) by wt.) is prepared with minimum warming and allowed to cool to constant temperature. The resin mixture (8.4 g) is added, the solution is stirred for five minutes, the mixture is filtered and the pH of the filtrate is the isoionic point pH of the protein.

The above-described modified proteins are used in compositions of the present invention in an amount such that the ratio of the total weight of surfactant to the weight of modified protein lies in the range from about 4:1 to about 500:1, preferably from about 10:1 to about 100:1, most preferably from about 10:1 to about 25:1.

Generally, the modified proteins may be present in the compositions of the invention in an amount up to 20%, but they are normally used in an amount between 0.5 and 10%, preferably between 1 and 4%, by weight of the composition.

Specific methods for making modified proteins useful in the present invention are described in the previously mentioned DOS No. 2434063 and are hereby specifically incorporated herein by reference.

(b) The Surfactants

It is an essential feature of the invention that the major proportion of the surfactant in the compositions is constituted by an alkyl benzene sulphonate in which the alkyl group contains from eight to eighteen carbon atoms in a straight or branched chain configuration and in which the cation may be an alkali metal, alkaline earth metal, ammonium or alkanolammonium radical. It has been found that the conditioning efficiency (i.e. level of benefit ÷ level of protein) of protein containing detergent compositions depends quite markedly on the weight ratio of the above detergent component to other auxiliary detergent components, and in particular that there is a significant increase in conditioning efficiency at a weight ratio greater than 1.5:1. Preferably, the weight ratio of these components should be greater than 1.8:1 and especially greater than 2.5:1. The upper limit of weight ratio is set by the adverse solubility characteristics associated with high proportions of alkyl benzene sulphonate, and the weight ratio should, therefore, be less than 10:1, preferably less than 5:1 and especially less than 4:1.

The auxiliary detergent components may be any one or more of the following:

(A) Anionic Soap and Non-Soap Synthetic Detergents

This class of detergents includes ordinary soaps such as the sodium, potassium, ammonium, alkyl ammonium and alkylolammonium salts of higher fatty acids containing from 8 to 24 carbon atoms and preferably from 10 to 20 carbon atoms. Suitable fatty acids can be obtained from natural sources, such as plant or animal esters (e.g. palm oil, coconut oil, babassu oil, soybean oil, castor oil, tallow, whale and fish oils, grease, lard, and mixtures thereof). The fatty acids also can be synthetically prepared (e.g. by the oxidation of petroleum or by hydrogenation of carbon monoxide by the Fischer Tropsch process). Resin acids are suitable, such as resin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium, potassium, and triethanol-ammonium salts of the mixtures of fatty acids derived from coconut oil and tallow, e.g. sodium or potassium tallow and coconut soaps.

This class of detergents also includes water-soluble salts, particularly the alkali metal salts, of organic sulphuric reaction products having in their molecular structure an alkyl radical containing from 8 to 24 carbon atoms and a sulphonic acid or sulphuric acid ester radical. (Included in the term alkyl is the alkyl portion of higher acyl radicals.) Examples of this group of synthetic detergents which form a part of the preferred compositions of the present invention are the alkali metal, e.g. sodium or potassium, alkyl sulphates, especially those obtained by sulphating the higher alcohols (8 to 24 carbon atoms) produced by reducing the glycerides of tallow or coconut oil; the alkali metal olefin sulphonates of from 8 to 24 carbon atoms described, for example, in U.S. Pat. No. 3,332,880 (incorporated herein by reference); and the alkali metal alkyl glyceryl ether sulphonates, especially those ethers of the higher alcohols derived from tallow and coconut oil.

Other anionic detergents include the sodium coconut oil fatty acid monoglyceride sulphates and sulphonates; salts of alkyl phenol ethylene oxide ether sulphates with 1 to 30 units of ethylene oxide per molecule and in which the alkyl radicals contain from 8 to 24 carbon atoms; the reaction product of fatty acids esterified with isethionic and neutralized with sodium hydroxide where, for example, the fatty acid is oleic or derived from coconut oil, sodium or potassium salts of fatty acid amides of a methyl tauride in which the fatty acids, for example, are derived from coconut oil; sodium or potassium $\beta$-acetoxy- or $\beta$-acetamidoalkanesulphonates where the alkane has from 8 to 22 carbon atoms; and others known in the art. A number are specifically set forth in U.S. Pat. Nos. 2,286,921; 2,486,922; and 2,396,278, the disclosures of which are incorporated herein by reference.

Other synthetic anionic detergents useful herein are alkyl ether sulphates. These materials have the formula $R^2O(C_2H_4O)_nSO_3M$ wherein $R^2$ is alkyl or alkenyl of about 8 to 24 carbon atoms, $n$ is 1 to 30, and M is a salt-forming cation selected from alkali metal, ammonium and dimethyl-, trimethyl-, triethyl-, dimethanol-, diethanol-, trimethanol- and triethanol- ammonium cations.

The alkyl ether sulphates are condensation products of ethylene oxide and monohydric alcohols having about 8 to 24 carbon atoms. Preferably, $R^2$ has 12 to 16 carbon atoms. The alcohols can be derived from fats, e.g. coconut oil or tallow, or can be synthetic.

Lauryl alcohol and straight-chain alcohols derived from tallow are preferred herein. Such alcohols are reacted with from 1 to 12, especially 6, molar proportions of ethylene oxide and the resulting mixture of molecular species, having, for example, an average of 6 moles of ethylene oxide per mole of alcohol, is sulphated and neutralized.

Specific examples of alkyl ether sulphates useful in the present invention are sodium coconut alkyl ethylene glycol ether sulphate; lithium tallow alkyl triethylene glycol ether sulphate; and sodium tallow alkyl hexaoxyethylene sulphate. Preferred herein for reasons of excellent cleaning properties and ready availability are the alkali metal coconut- and tallow-alkyl oxyethylene ether sulphates having an average of 1 to 10 oxyethylene moieties per molecule. The alkyl ether sulphates are described in U.S. Pat. No. 3,332,876, the disclosures of which are specifically incorporated herein by reference.

(B) Nonionic Synthetic Detergents

Nonionic synthetic detergents may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of 'Pluronic.' These compounds are formed by condensing ethylene oxide with a hydrophobic base formed by the condensation of propylene oxide with propylene glycol. The hydrophobic portion of the molecule which, of course, exhibits water-insolubility, has a molecular weight of from 1500 to 1800. The addition of polyoxyethylene radicals to this hydrophobic portion tends to increase the water solubility of the molecule as a whole and the liquid character of the product is retained up to the point where the polyoxyethylene content is about 50% of the total weight of the condensation product.

Other suitable nonionic synthetic detergents include the following:

1. The polyethylene oxide condensates of alkylphenol, e.g. the condensation products of alkyl phenols having an alkyl group containing from 6 to 12 carbon atoms in either a straight-chain or branched-chain configuration, with ethylene oxide, the said ethylene oxide being present in amounts equal to 5 to 30 moles of ethylene oxide per mole of alkyl phenol. The alkyl substituent in such compounds may be derived, for example, from polymerised propylene, diisobutylene, octene or nonene. Preferred examples of this type include nonyl phenol condensed with 10, 20 or 30 moles of ethylene oxide, dinonyl phenol condensed with 2 moles of ethylene oxide and diisooctyl phenol condensed with 15 moles of ethylene oxide.

2. Those derived from the condensation of ethylene oxide with the product resulting from the reaction of propylene oxide and ethylene diamine. Examples are compounds containing from 40% to 80% polyoxyethylene by weight and having a molecular weight of from 5,000 to 11,000 resulting from the reaction of ethylene oxide groups with a hydrophobic base constituted of the reaction product of ethylene diamine and excess propylene oxide. Bases having a molecular weight of the order of 2,500 to 3,000 are satisfactory.

3. The condensation product of aliphatic alcohols having from 8 to 24 carbon atoms, in either straight-chain or branched-chain configuration with ethylene oxide, e.g. a coconut alcohol-ethylene oxide condensate having from 5 to 30 moles of ethylene oxide per mole of coconut alcohol, the coconut alcohol fraction having from 10 to 14 carbon atoms. Particularly preferred are the condensation products of coconut alcohol with an average of either about 5.5 or about 15 moles of ethylene oxide per mole of alcohol, the condensation product of about 15 moles of ethylene oxide with one mole of tridecanol, and myristyl alcohol condensed with 10 moles of ethylene oxide per mole of alcohol.

4. A detergent having the formula $R^3R^4R^5N \rightarrow O$ (amine oxide detergent) wherein $R^3$ is an alkyl group containing from 10 to 28 carbon atoms, from 0 to 2 hydroxy groups and from 0 to 5 ether linkages, there being at least one moiety of $R^3$ which is an alkyl group containing from 10 to 18 carbon atoms and 0 ether linkages, and $R^4$ and $R^5$ are each selected from alkyl radicals and hydroxyalkyl radicals containing from 1 to 3 carbon atoms.

Specific examples of amine oxide detergents include: dimethyldodecylamine oxide, dimethyltetradecylamine oxide, ethylmethyltetradecylamine oxide, cetyldimethylamine oxide, dimethylstearylamine oxide, cetylethylpropylamine oxide, diethyldodecylamine oxide, diethyltetradecylamine oxide, dipropyldodecylamine oxide, bis-(2-hydroxyethyl) dodecylamine oxide, bis-(2-hydroxyethyl)-3-dodecoxy-1-hydroxypropylamine oxide, (2-hydroxypropyl)methyltetradecylamine oxide, dimethyloleylamine oxide, dimethyl-(2-hydroxydodecyl) amine oxide, and the corresponding decyl, hexadecyl and octadecyl homologues of the above compounds.

5. A detergent having the formula

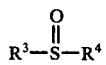

wherein $R^3$ and $R^4$ are as defined above. Specific examples of sulphoxide detergents include dodecyl ethyl sulphoxide, tetradecyl methyl sulphoxide, 3-hydroxytridecyl methyl sulphoxide, 3-methoxytridecyl methyl sulphoxide, 3-hydroxy-4-dodecoxybutyl methyl sulphoxide, octadecyl 2-hydroxyethyl sulphoxide and dodecylethyl sulphoxide.

6. The ammonia, monoethanol and diethanol amides of fatty acids having an acyl moiety of from 8 to 18 carbon atoms. These acyl moieties are normally derived from naturally occurring glycerides, e.g. coconut oil, palm oil, soybean oil and tallow but can be derived synthetically, e.g. by the oxidation of petroleum, or by hydrogenation of carbon monoxide by the Fischer Tropsch process.

(C) Ampholytic Synthetic Detergents

Ampholytic synthetic detergents can be broadly described as derivatives of aliphatic or aliphatic derivates of heterocyclic secondary and tertiary amines, in which the aliphatic radical may be straight-chain or branched and wherein one of the aliphatic substituents contain from 8 to 18 carbon atoms and at least one contains an anionic water-solubilizing group, e.g. carboxy, sulpho or sulphato. Examples of compounds falling within this definition are sodium 3-(dodecylamino)-propionate, sodium 3-(dodecylamino) propane-1-sulphonate, sodium 2-(dodecylamino)-ethylsulphate, sodium 2-(dimethylamino)-octadecanoate, disodium 3-(N-carboxymethyl dodecylamino)-propane-1-sulphonate, disodium octadecyl-iminodiacetate, sodium 1-carboxymethyl-2-undecyl imidazole, and sodium N,N-bis-(2-hydroxyethyl)-2-sulphato 3-dodecoxypropylamine.

(D) Zwitterionic Synthetic Detergents

Zwitterionic synthetic detergents can be broadly described as derivatives of aliphatic quaternary ammonium and phosphonium or tertiary sulphonium compounds, in which the cationic atom may be part of a heterocyclic ring, and in which the aliphatic radical may be straight-chain or branched and wherein one of the aliphatic substituents contains from 3 to 18 carbon atoms, and at least one aliphatic substituent contains an anionic water-solubilizing group, e.g. carboxy, sulpho or sulphato.

Particularly preferred detergents within this class have the formula:

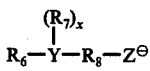

where $R_6$ is alkyl, alkenyl or hydroxyalkyl containing from 8 to 18 carbon atoms and optionally up to 10 ethylene oxide moieties and/or a glyceryl moiety; Y is nitrogen, phosphorus or sulphur; $R_7$ is alkyl or monohydroxyalkyl containing 1 to 3 carbon atoms; $x$ is 1 when Y is S, 2 when Y is N or P; $R_8$ is alkylene or hydroxyalkylene containing from 1 to 5 carbon atoms; and Z is a carboxy, sulphonate, sulphate, phosphate or phosphonate groups.

Examples of compounds within this definition are 3-(N,N-dimethyl-N-hexadecyl-ammonio)-2-hydroxypropane-1-sulphonate, 3-(N,N-dimethyl-N-hexadecylammonio)-propane-1-sulphonate, 2-(N,N-dimethyl-N-dodecylammonio)acetate, 3-(N,N-dimethyl-N-dodecylammonio)propionate, 2-(N,N-dimethyl-N-octadecylammonio)-ethyl sulphate, 2-(S-methyl-S-tert.hexadecyl-sulphonio)ethane-1-sulphonate, 3-(S-methyl-S-dodecylsulphonio) propionate, 4-(S-methyl-S-tetradecylsulphonio) butyrate, 2-(trimethylammonio)octadecanoate, and 3-(N,N-bis-(2-(hydroxyethyl)-N-octadecylammonio)-2-hydroxy propane-1-sulphonate and 3-(N,N-dimethyl-N-1-methyl alkyl ammonio)-2-hydroxypropane-1-sulphonate, wherein alkyl averages 13.5 to 14.5 carbon atoms in length. Some of these detergents are described in U.S. Pat. Nos. 2,129,264; 2,178,353; 2,774,786; 2,813,898 and 2,828,332, which are hereby incorporated herein by reference.

The soap and non-soap anionic, nonionic amphoteric and zwitterionic detergents surfactants mentioned above can be used as the sole auxiliary surface-active agents, or the various examples may be mixed when used in the practice of the invention. Especially preferred are anionic and nonionic surface-active agents. The total amount of surface-active agent incorporated in the preparation depends upon the intended use of the particular formulation. Thus it will relate to the weight of the preparation as a whole, when it is applied directly to skin or hair, e.g. as a shampoo, or the concentration at which it will be used as a solution in, for example, dishwashing water or bath water. In most cases a content within the range of 5 to 50% by weight of the preparation is suitable. More particularly, detergent compositions for cleaning purposes will generally comprise between 10 and 45% of surface active agent.

The invention is applicable to a variety of detergent compositions which may come into contact with keratin in the normal course of use, for example dishwashing liquids, hair shampoos, bathing compositions, heavy-duty detergent compositions, hard-surface-cleaning compositions and bar soaps. The physical form of the composition may vary widely, from granular solids, through gels and creams, to viscous or mobile liquid compositions. Dishwashing compositions are generally liquid and comprise mixtures of water and foaming detergents. Granular detergent compositions on the other hand, may contain little or no free water.

The preferred liquid detergent compositions for use, for instance, as dishwashing compositions or shampoos, comprise between 20 and 40% by weight of foaming detergent. More especially, the foaming detergent comprises:

(a) from 10 to 36% by weight, preferably from 20 to 30% by weight of an alkyl benzene sulphonate in which the alkyl group contains from 10 to 14 carbon atoms;

(b) from 2 to 16%, preferably from 5 to 10% of a water-soluble hydrocarbon sulphate of the general formula $R^2O(C_2H_4O)_nSO_3M$ wherein $R^2$ is a straight or branched, saturated or unsaturated aliphatic, hydrocarbon radical having from 12 to 16 carbon atoms, or a benzene radical substituted with an aliphatic, straight or branched hydrocarbon group having from 10 to 14 carbon atoms; $n$ is from 1 to 12; and M is an alkali metal, ammonium or dimethyl-, trimethyl-, triethyl-, dimethanol-, diethanol-, trimethanol- or triethanol- ammonium cation;

(c) up to 10% by weight of an ammonia, monoethanol or diethanol amide of a fatty acid having an acyl moiety of from 8 to 18 carbon atoms; and (d) up to 10% by weight of the condensation product of from 3 to 25 moles of an alkylene oxide, preferably ethylene or propylene oxide, and one mole of an organic, hydrophobic compound, aliphatic or alkyl aromatic in nature, the latter having from 8 to 24 carbon atoms.

Additional Components

The liquid detergent or gel compositions of the invention generally comprise a carrier based upon water and/or a water-soluble solvent. Suitable solvents include $C_{2-8}$ mono and di-alcohols, e.g. ethanol, butanol, methyl propanol-1 and -2, amylol or pentanol, butanediol, toluol, benzyl carbinol, ethyleneglycol monobutyl ether, propyleneglycol propyl ether and diethyleneglycol dimethyl ether. They are generally present in amounts up to 15% by weight of the composition. Additional components of liquid detergent compositions include buffer materials, foam boosters, such as $C_{12}$–$C_{14}$ alkyl,di $C_1$–$C_3$ alkyl amine oxides and $C_1$–$C_3$ alkylolamides of $C_{10}$–$C_{14}$ carboxylic acids, thickeners, preservatives, opacifiers, perfumes, dyes, fluorescers, tarnish inhibitors, bactericides, hydrophobic oily materials and hydrotropes. Commonly employed hydrotropes include conventional lower alkylaryl sulphonates such as sodium and potassiume toluene sulphonate, xylene sulphonate, benzene sulphonate and cumene sulphonate. Urea and lower alkanol hydrotropes such as methanol, ethanol, propanol and butanol may also be used.

Hydrophobic oily materials suitable for use in the present invention include animal, vegetable and mineral oils and waxes, for example beeswax, spermaceti and carnauba wax; fatty alcohols such as stearyl, myristyl and cetyl alcohols; fatty esters and partial esters such as isopropyl myristate and glyceryl monostearate; fatty acids such as stearic acid; lanolin and cholesterol derivatives; and silicone oils. The compositions of the invention may also comprise components designed to enhance the moisturizing effectiveness of the compositions. Suitable components include lower aliphatic alcohols having from 2 to 6 carbon atoms and 2 to 3 hydroxy groups, for example 1,4 butanediol, 1,2-propylene glycol and glycerine. Other suitable components include urea or urea derivatives such as guanidine, pyrrolidone or allantoin.

Solid granular detergent compositions may contain foam enhancers, foam depressants, bleaches, anti-redeposition agents, enzymes, enzyme and bleach activators, fluorescers, builders and other normal components of granular detergent compositions. Solid compositions in bar form may also contain additives such as fatty acids, salts, skin creams and oils.

As mentioned previously, the optimum choice of protein for any particular composition depends to a certain extent upon the pH of the composition in use, i.e. the pH of the carrier upon application to keratin. The in-use pH of the compositions of the invention may vary widely, of course, depending upon the purpose and manner of use of the compositions. Liquid compositions designed for shampoos are generally applied to hair in medium/high concentration aqueous solution, and the in-use pH is close to the pH of the composition itself. This may be any pH in the range, generally, from 4 to 9. Detergent compositions such as liquid dishwashing compositions, bathing compositions and heavy-duty granular or liquid detergents are usually used in a large excess of water, and the in-use pH is the pH of an aqueous solution of the composition at a concentration generally in the range from 0.01% to 2% by weight. Builder-free detergent compositions used, for instance, as light-duty detergents generally have an in-use pH of about 7; built heavy-duty detergents generally have an in-use pH in the alkaline range up to a pH of about 11. Soap bar compositions are applied to skin as an aqueous solution or dispersion of the soap bar ingredients at a concentration, generally in the range from 5 to 15 wt%. The pH of the soap dispersion may vary, depending upon the type of soap bar employed, from a pH of 5.5 to about 10.5.

Conditioning Tests

Conditioning performance was measured in both in-vitro and in-vivo tests, a high degree of correlation between the various test methods being found. The in-vitro test (called the calf-skin occlusivity test) was based upon the rate of water transpiration through a sample of calf-skin brought into contact with a 0.15% aqueous solution of a detergent composition (at 18° hardness) containing the protein. The occlusivity of the protein was measured as the percentage reduction in the rate of water transpiration for the proteinaceous surfactant solution compared with that for water.

EXAMPLES I TO III

Liquid detergent compositions falling within the scope of the present invention, are shown as Examples I to III in the adjoining chart. The conditioning effectiveness of these compositions, measured as the percentage reduction in the rate of water transpiration in both in-vitro and in-vivo tests, is also recorded. Corresponding data is given for compositions having a lower ratio of alkyl benzene sulphonate to fatty alcohol sulphate (Standards I to III). It may be seen that the conditioning effectiveness of the compositions of the invention is significantly greater than that of corresponding standard compositions for any given protein level, and that this is particularly true at lower protein levels. As a result, the invention enables conditioning performance to be sustained at a reduced protein level and with minimum alteration to the physical characteristics of the base detergent formula.

| COMPOSITION | EXAMPLES | | | STANDARDS | | |
|---|---|---|---|---|---|---|
| | I | II | III | I | II | III |
| Ammonium linear $C_{12}$-$C_{14}$ alkyl benzene sulphonate | 27.6 | 27.6 | 27.6 | 18.4 | 18.4 | 18.4 |
| Sodium linear $C_{12}$-$C_{14}$ alcohol sulphate including 3 ethylene oxide moieties | 9.2 | 9.2 | 9.2 | 18.4 | 18.4 | 18.4 |
| Lauric monoethanolamide | 2.0 | 2.0 | 2.0 | 2.0 | 2.0 | 2.0 |
| Industrial Methylated Spirits | 11.0 | 11.0 | 11.0 | 11.0 | 11.0 | 11.0 |
| Magnesium chloride | 2.1 | 2.1 | 2.1 | 2.1 | 2.1 | 2.1 |
| Hydroxybutylated gelatin - Mol.wt. 28,000 - pI 9.3 | 3.0 | 2.0 | 1.5 | 4.0 | 3.0 | 2.0 |
| Water | To 100 | To 100 | To 100 | To 100 | To 100 | To 100 |
| PERFORMANCE | | | | | | |
| In-vitro (Percentage reduction of water transpiration) | 13 | 8 | 6 | 8 | 2 | — |
| In-vivo (Percentage reduction of water transpiration) | 27 | 20 | 18 | 22 | 9 | −2 |

EXAMPLE IV

Three liquid detergent products were made up having the following compositions. Product A was a conventional formulation not containing a modified protein, Product B was similar to Product A but containing protein, and Product C was in accordance with the invention.

| Ammonium $C_{12}$ linear alkyl benzene sulphonate | 18.4 | 18.4 | 27.6 |
|---|---|---|---|
| Sodium triethoxy $C_{12}$ alkyl sulphate | 18.4 | 18.4 | 9.2 |
| $C_{12}$ monoethanolamide | 4.2 | 1.9 | 1.9 |
| Ethyl Alcohol | 13.0 | 11.0 | 11.0 |
| Butoxylated base hydrolysed gelatin Molecular wt. 28,000 | — | 3.49 | 1.5 |
| $MgCl_2 \, 6H_2O$ | — | 2.1 | 2.1 |
| Urea | — | — | 2.0 |
| Water | To 100 | To 100 | To 100 |

Each product was then used for a 3-week period by a panel of housewives whose hands were graded for skin condition before and after the usage period. The design of the test took into account differences in hand condition at the start of the test in order to ensure that each product was exposed to the same range of hand condition.

Results were as follows, expressed as an improvement in hand condition during the Test:

| | A | 0.000 |
|---|---|---|
| Product | B | 0.140 |
| | C | 0.150 |
| | $T_{95} =$ | 0.144 |

It can be seen that the product C in accordance with the invention provides an equivalent benefit to product B containing twice the level of protein in a conventional formulation and is significantly better than the non-protein control product A.

What is claimed is:

1. A foaming and conditioning detergent composition having an enhanced mildness effect towards keratin comprising:
    (a) from about 5 to about 50% by weight of the composition of a surfactant combination which is:

(i) an alkylbenzene sulfonate salt in which the alkyl group is selected from the group consisting of straight chain and branched chain alkyl groups containing from eight to eighteen carbon atoms and in which the cation is selected from the group consisting of alkali metal, alkaline earth metal, ammonium and alkanolammonium radicals;

(ii) an auxiliary surfactant selected from the group consisting of synthetic anionic surfactants other than those defined in (i) above, natural anionic surfactants, nonionic surfactants, amphoteric surfactants, zwitterionic surfactants and mixtures thereof;

(b) from about 0.5 to about 10% by weight of the composition of a modified protein having a molecular weight greater than about 5,000 l and having an isoionic point (pI) greater than about pH 6, said modified protein being a hydroxyalkylated gelatin; and (c) the balance of the composition comprising a carrier;

wherein the weight ratio of (i) to (ii) is from about 1.5:1 to about 10:1 and wherein the weight ratio of (a) to (b) is from about 4:1 to about 500:1.

2. A composition according to claim 1 wherein the weight ratio of (i) to (ii) is from about 1.8:1 to about 5:1.

3. A composition according to claim 2 wherein said modified protein is a hydroxybutylated gelatin and wherein the molecular weight is from about 20,000 to about 100,000.

4. A composition according to claim 3 wherein the weight ratio of (i) to (ii) is from about 2.5:1 to about 4:1.

5. A composition according to claim 4 wherein the weight ratio of (a) to (b) is from about 10:1 to about 100:1.

6. A composition according to claim 5 wherein the auxiliary surfactant is a water soluble anionic surfactant having the formula

$$R^2O(C_2H_4O)_nSO_3M$$

wherein $R^2$ is selected from the group consisting of straight and branched chain, saturated and unsaturated aliphatic hydrocarbon radicals having from about 12 to about 16 carbon atoms, $n$ is a number from 0 to about 12 and M is a cation selected from the group consisting of alkali metal, alkaline earth metal, ammonium and substituted ammonium radicals.

7. A foaming and conditioning liquid detergent composition having an enhanced mildness effect towards keratin comprising:

(a) from about 10 to about 45% by weight of the composition of a surfactant combination which is:

(i) an alkylbenzene sulfonate salt in which the alkyl group is selected from the group consisting of straight chain and branched chain alkyl groups consisting from eight to eighteen carbon atoms and in which the cation is selected from the group consisting of alkali metal, alkaline earth metal, ammonium and alkanolammonium radicals;

(ii) an auxiliary surfactant selected from the group consisting of synthetic anionic surfactants other than those defined in (i) above, natural anionic surfactants, nonionic surfactants, amphoteric surfactants, zwittionic surfactants and mixtures thereof;

(b) from about 0.5 to 10% by weight of the composition of a modified protein having a molecular weight of from 5,000 to about 100,000 and an isoionic point (pI) greater than about pH 7.2, said modified protein being a hydroxyalkylated gelatin; and (c) the balance of the composition comprising a liquid carrier comprising water, mono- and dihydric alcohols containing from 2 to 8 carbon atoms and mixtures thereof;

wherein the weight ratio of (i) to (ii) is from about 1.8:1 to about 5:1 and wherein the weight ratio of (a) to (b) is from about 10:1 to about 100:1.

8. A composition according to claim 7 wherein said modified protein is a hydroxybutylated gelatin.

9. A composition according to claim 8 wherein the auxiliary surfactant is a water soluble anionic surfactant having the formula

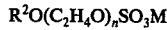

$$R^2O(C_2H_4O)_nSO_3M$$

wherein $R^2$ is selected from the group consisting of straight and branched chain, saturated and unsaturated aliphatic hydrocarbon radicals having from about 12 to about 16 carbon atoms, $n$ is a number from 0 to about 12 and M is a cation selected from the group consisting of alkali metal, alkaline earth metal, ammonium and substituted ammonium radicals.

10. A composition according to claim 9 wherein the molecular weight of the modified protein is from about 20,000 to about 100,000 and wherein the isoionic point (pI) of the modified protein is greater than about pH 8.0.

* * * * *